United States Patent [19]
Nanji

[11] Patent Number: 5,413,785
[45] Date of Patent: May 9, 1995

[54] METHODOLOGY EMPLOYING LACTOBACILLUS GG FOR REDUCTION OF PLASMA ENDOTOXIN LEVELS CIRCULATING IN-VIVO

[75] Inventor: Amin A. Nanji, Wellesley, Mass.

[73] Assignee: New England Deaconess Hospital Corp., Boston, Mass.

[21] Appl. No.: 206,031

[22] Filed: Mar. 3, 1994

Related U.S. Application Data

[63] Continuation of Ser. No. 9,647, Jan. 27, 1993, abandoned.

[51] Int. Cl.⁶ ............................................. A61K 37/00
[52] U.S. Cl. ............................. 424/93.45; 424/93.4; 435/853; 435/854
[58] Field of Search .................. 424/93 R, 93 D, 93 J, 424/93.45, 93.4; 435/853, 854

[56] References Cited

U.S. PATENT DOCUMENTS

| | | | |
|---|---|---|---|
| 4,839,281 | 6/1989 | Gorbach et al. | 424/93 J |
| 5,032,399 | 7/1991 | Gorbach et al. | 424/93 J |

OTHER PUBLICATIONS

Wells, C. L., et al., "Circulatory Shock" vol. 37, 1992, pp. 117–123.
Goldin, B. R., et al., "Digestive Diseases and Sciences" vol. 37, #1, Jan. 1992, pp. 121–128.
Gorbach, S. L., "Ann. Med.," vol. 22, 1990, pp. 37–41.
Gilliland, S. E., "Fems Microbiology Rev.," vol. 87, 1990, pp. 175–188.
Klebanoff, S. J., et al., "The Journal of Infectious Diseases," vol. 164, 1991, pp. 94–100.
Rammelsberg, M., et al., "Journal of Applied Bacteriology," vol. 69, 1990, pp. 177–184.
Silva, M., et al., "Antimicrobial Agents and Chemotherapy," vol. 31 (8), Aug. 1987, pp. 1231–1233.
Garbach, S. L., et al., "The Lancet," vol. 1, Dec. 26, 1987, p. 1519.
Thompson, G. E., "Journal of Environmental Pathology and Toxicology" vol. 10, 1977, pp. 113–123.

*Primary Examiner*—David M. Naff
*Assistant Examiner*—Kristin Larson
*Attorney, Agent, or Firm*—David Prashker

[57] ABSTRACT

A method is provided for reducing the quantity of endotoxin circulating in the blood plasma of a living subject affected by an endotoxin-mediated clinical state. The method employs a formulated preparation comprising at least one persistent, acid-resistant, and colonizing Lactobacillus species in combination with a biocompatible carrier. The user then introduces the formulated preparation to the gastrointestinal tract of the subject on one or on multiple occasions.

8 Claims, 2 Drawing Sheets

METHODOLOGY EMPLOYING LACTOBACILLUS GG FOR REDUCTION OF PLASMA ENDOTOXIN LEVELS CIRCULATING IN-VIVO

This application is a continuation of application Ser. No. 08/009,647, filed Jan. 27, 1993, now abandoned.

RESEARCH SUPPORT

The research effort for the present invention was supported by grants from the Milton Fund and from the New England Deaconess Hospital.

FIELD OF THE INVENTION

The present invention is concerned generally with effective methods for reducing the quantity of endotoxins circulating within the plasma in,vivo; and is particularly concerned with efficacious methods for therapeutically treating specific endotoxin-mediated pathological conditions and afflictions such as alcoholic liver disease in a particular living subject.

BACKGROUND OF THE INVENTION

Endotoxins by definition are lipopolysaccharides or "LPS" constituents of the outer membrane of gram-negative bacteria. All endotoxins comprise a polysaccharide portion and a covalently bound lipid component called "lipid A"; and hence, they are chemically lipopolysaccharides. In common practice and in clinical practice, the terms "endotoxin" and "lipopolysaccharide" are often used interchangeably and synonymously; but in its strict denotative meaning, an endotoxin represents a complexed association of LPS with other outer membrane biochemical compositions and structures [Rietschel et al., Scan. J. Infect. Dis. (Suppl.) 31:8-21 (1982); Westphal et al., Advances In Immunopharmacology, Pergammon Press, 1985; Van DeVenter et al., Gastroenterology 94:825-831 (1988); and Reitschel et al., Infectious Disease Clinics Of North America 5:753-779 (1991)].

Endotoxins were first discovered and identified at the end of the 19th century when it was found that lysates of heat-inactivated Vibrio cholerae contained a toxic component which was capable of inducing shock and death in experimental animals. This heat-stable toxic was termed "endotoxin" to distinguish it from the heat-labile "exotoxins" which were actively secreted by the live bacteria. About the same time, other scientists independently isolated the same toxin and made two important contributions: First, it was observed that this endotoxin could be isolated from lysates of many different gram-negative bacteria, but never from similar preparations of gram-positive bacteria. Second, the remarkable pyrogenic properties of endotoxins were demonstrated. However, it was only in 1935 that research investigators, using a method of trichloracetic extraction, determined that the endotoxic activity of gram-negative bacterial lysates resides in an outer-membrane macromolecular complex of protein, lipid and polysaccharide. Twenty years later, the now classic studies and biochemical investigations of endotoxin were performed—which demonstrated that protein-free lipopolysaccharide possessed all the properties of the earlier prepared, crude endotoxin.

A detailed knowledge of the biochemistry of the cell wall of gram-negative bacteria is helpful in understanding the structural basis of the toxicity and also of the rationale for the conventionally known approaches to treatment of endotoxic shock. The cell wall of gram-negative bacteria is a complex structure composed of the innermost cytoplasmic membrane, the periplasm, the peptidoglycan layer, the outer membrane, and, in many instances, additional structures such as capsules, extracellular polysaccharide, fimbriae and flagella [Bayston, K. F. and J. Cohen, J. Med. Microbiol. 31:73-83 (1990)]. Endotoxin (LPS) is found exclusively in the outer membrane; and, specifically, only in the outer leaflet of this membrane. Here, LPS forms a hydrophobic barrier which restricts the entry of noxious substances such as bile salts, digestive enzymes and certain antibiotics; and enables the living bacterium to evade many innate host-defense factors including complement, lysozyme and cationic proteins. Endotoxin may also be found in a cell-free form which occurs after bacterial autolysis; as a result of exposure to cell-membrane toxins or antibiotics; during rapid (log-phase) growth; or when essential nutrients are depleted from the environment. All of these conditions typically arise during septicaemia [Brogden, K. A. and M. Phillips, Electron. Microsc. Rev. 1:261-277 (1988); Flynn et al., Infect. Immun. 56:2760-2762 (1988); and Shenep et al., J. Infect. Dis. 157:565-568 (1988)].

Endotoxins have been implicated in the pathogenesis of a variety of different clinical disorders. A representative, but incomplete listing of abnormal clinical conditions and specific disease states is given by Table A below.

TABLE A

| Disease Association | Reference |
| --- | --- |
| Septic shock, sepsis, infections. | Gorelick et al., Infect Dis. Clin. N. Amer. 5:899-913 (1991). |
| Various forms of liver disease; e.g. - viral hepatitis, alcoholic liver injury, liver failure, cirrhosis, obstructive jaundice, toxic livery injury; total parenteral nutrition associated. | Nolan, J. P., Immunological Investigations 18:325-337 (1989). Nolan, J. P. Hepatology 10:887-891 (1989); Pappo et al., J. Parent. Enteral. Nutr. 16:529-532 (1992). |
| Bowel disease; e.g. - Crohn's disease, ulcerative colitis, ischemia, bowel obstruction, ilueus. | Aoki, K., Acta Med Okayama 32:207-216 (1978). Papa et al., J Surg Res 35: 264-269 (1983). Rosher et al., Am J Surg 155:348-355 (1988). |
| Kidney disease; e.g. - acute renal failure, glomerulonephritis. | Wardle, E. N., Quart. J. Med. 44:389-398 (1975). Tomosugi et al., Immunobiology 175:104 (1987). |
| Lung disease; e.g. - adult respiratory distress syndrome, pneumonia. | Brigham, K. L., Am. Rev. Resp. Dis. 133:913-927 (1986). |
| Trauma; e.g. - abdominal/chest trauma, surgery, colonoscopy. | Kelley, et al., Surg. Gynecol-Obstet. 161:332-334 (1985). |
| Radiation injury. | Maxwell, et al., Lancet 1:1148-1149 (1986). |
| Graft versus host disease. | Moore, et al., Transplantation 43:731-736 (1987). |
| Toxic-shock syndrome. | Stone, et al., J. Infect. Dis. 155:682-689 (1987). |
| Immunocompromised patients with fever. | Harris, et al., J. Clin. Pathol. 37:467-70 (1984). |
| Neonatal necrotizing enterocolitis. | Schiefe, et al., Am. J. Clin. Pathol. 83:227-229 (1985). |
| Acute pancreatis | Exley, et al., Gut. 33:116-1128 (1992). |
| Liver transplantation | Yokoyama, et al., Transpl. Proc. 21:3833-3841 (1989); Miyata, et al., Lancet 2:189-191 (1989). |
| Heat stroke | Anon, Lancet 2:1137-1138 |

| TABLE A-continued |  |
|---|---|
| Disease Association | Reference |
| | (1989). |

Of the representative abnormal clinical conditions and disease states mediated by endotoxins, gram-negative septic shock is probably the most familiar to physicians and is the setting in which the role of endotoxin is most clearly established by empirical evidence [Morrison, D. C. and J. L. Ryan, *Ann. Rev. Med.* 38:417-432 (1987)]. Septic shock is estimated to occur in about 20-40% of patients with gram-negative septicaemia. Of these, about 75% die despite the use of potent antibiotics and intensive-care facilities—the rationale for this phenomenon being that while antibiotics are very effective at killing bacteria, these compositions have no activity against endotoxins or the host-derived factors which are now thought to mediate the toxic effects of endotoxin [Bayston, K. F. and J. Cohen, *J. Med. Microbiol.* 31:73-83 (1990) and the references cited therein].

Another major area of research investigations regarding the physiological and pharmacological effects of endotoxins is alcoholic liver disease. The role of endotoxin in alcoholic liver disease, hepatic failure, and hepatic necrosis secondary to toxic and infectious agents has been recognized for many years. Representative of these research investigations are the following publications: Formal et al., *Proc. Soc. Exp. Biol. Med.* 103:451-418 (1960); Galanos et al., *Proc. Natl. Acad. Sci. U.S.A.* 76:939-943 (1979); Camara et al., *Proc. Soc. Exp. Biol. Med.* 172:255-259 (1983); Nolan J. P. and D. S. Camaria, *Immun. Invest.* 18:325-337 (1989); Shibayana et al., *Exp. Mol. Pathol.* 55:196-202 (1991); Rutenburg et al., *J. Exp. Med.* 106:1-13 (1957); Broitman et al., *J. Exp. Med.* 119:633-641 (1964); Nolan, J. P. and N. V. Ali, *Proc. Soc. Exp. Biol. Med.* 129:29-31 (1968); Bhagwandeen et al., *J. Pathol.* 151:47-53 (1987); Arai et al., *Hepatology* 9:846-851 (1989); Nolan, J. P., *Hepatology* 10:887-891 (1989); Van Leeuwen et al., *Surgery* 110:169-175 (1991); Nanji et al., *AASLD A*859 (April 1992).

One of the curiosities regarding endotoxins clinically and physiologically are those areas and organs in which endotoxin is typically present or explicitly absent in the normal living individual—in comparison to those tissues and organs where endotoxins are manifestly present during the abnormal or pathological disease state in a living subject. Endotoxin is usually present in large quantities in the gastro-intestinal tract in the normal condition. No harmful effects are produced; and endotoxin is either not detectable or is present in extremely low concentrations (<10 pg/ml) in the circulating plasma or serum of healthy individuals. Even the intentional ingestion and introduction of milligram quantities of endotoxin fails to produce adverse reactions in healthy subjects [Bayston, K. F. and J. Cohen, *J. Med, Microbiol.* 31:73-83 (1990)]. This is believed to be due largely to the fact that the gut mucosa of healthy living individuals is both impervious to and resistant to the effects of intestinal endotoxins.

In general, however, there are three routes by which endotoxins (LPS) enter the tissues and organs of the body. These are: via the portal vein; by direct transmural absorption into the systemic blood stream; or by the intestinal lymphatics. Of these, the first two routes are considered the most important in man. Thus, if the gastrointestinal mucosa, and portal circulation, and hepatic-reticuloendotheoil system are intact, endotoxins do not appear in the blood stream and do not cause damage to organs and tissues. In contrast, the reported empirical evidence has revealed that if the gut is damaged or made permeable by any number of different events or disease states, endotoxins will transmigrate through the bowel mucosa [Aoki, K. A., *Acta. Med. Okayama* 32:207-216 (1978); Papa et al., *J. Surg. Res.* 35:264-269 (1983); Walker, R. I., *Exp. Hematol.* 6:172-184 (1978)]. Thus, if the gut is damaged or there is increased mucosal permeability of endotoxin secondary to systemic disease, endotoxin levels in blood will increase and give rise to the systemic effects associated with endotoxemia. Accordingly, symptoms typical of endotoxemia such as fever, hypotension, respiratory distress, hypercoagulability, and cholestasis, which complicate many inflammatory and ischemic diseases of the bowel as well as other disorders, are thought to be due to enhanced resorption of endotoxins [Van DeVenter et al., *Gastroenterology* 94:825-831 (1988)]. There is also considerable evidence that the transmigration of endotoxin through the gut is a commonly shared event which occurs in many different disease states. These include: bowel ischemia; peritonitis; total body irradiation consequences; colitis; portal vein occlusion; various forms of acute and chronic liver diseases; Crohn's disease; ulcerative colitis; necrotizing enterocolitis; and systemic infections of children and adults.

A number of widely used methods of varying sensitivity for detecting endotoxin are known. Perhaps the most widely used and most sensitive method is the Limulus amoebocyte lysate (LAL) assay [Jorgenson, J. H., *Handbook of Endotoxin* (Proctor, R. A., editor), volume 4, Elsevier, Amsterdam, 1986, page 1270; Yokota et al., *J. Biochem. Biophys. Meth.* 18:97-104 (1989)]. The principle of this assay is that gelation occurs when a sample containing endotoxin causes activation of a series of primitive enzymes present in the lysate of the horseshoe crab, *Limulus polythemus*. All the factors necessary for activation of the clotting process are found within the granules called amoebocytes; and with a lysate of the cells, a simple, gel-clot test able to detect picogram quantities of endotoxin is available.

In addition to the gel-clot method, several other variant assay methods for the detection of endotoxin have been introduced. These are based upon endotoxin-induced LAL activation; or upon turbidimetric and nephelometric measurements of the gelation reaction; or a determination of the protein content of the gel clot; or upon rocket immunoelectrophoresis; or on a direct measurement of the action of activated clotting enzyme on a synthetic chromogenic substrate.

The recognized high incidence of endotoxin mediated injury in vivo, and the all-too frequent mortality associated therewith, have led to investigations of therapeutic treatments and options. Among the reported investigations and attempts to neutralize the effects of endotoxin, three general forms of therapy for counteracting the effects of endotoxin have been pursued. These are: neutralizing the effect of endotoxin on macrophage mediators; decreasing intestinal production and absorption of endotoxin; and using monoclonal antibodies specific for endotoxin. Details for each of these three individual strategies and approaches are presented by Table B below.

TABLE B (a). Neutralizing the effect of endotoxin on macrophage mediators
1. Blockade of arachidonic acid metabolism, e.g.—cyclooxygenase and lipoxygenase inhibitors, inhibitors of tumor necrosis factor, platelet activating factor [Schirmer et al., *Curr. Surg.* 44:102 (1987); Revhaug et al., *Arch Surg.* 123:162 (1988)].
2. Antiproteases: infusion of antiproteases such as activated protein C and antithrombin III to counteract the effect of protease release by activated phagocytic cells [Emerson et al., *Am. J. Med.* 87:275 (1989); Taylor et al., *J. Clin. Invest.* 79:913 (1987)].
3. Pentoxyfylline/naloxone: mechanisms unknown [Ishizaka et al., *Am. Rev. Respir. Dis.* 138:376 (1988); Hacksaw et al., *Crit. Care Med.* 1848 (1990)].

(b). Decrease of intestinal production and absorption of endotoxin
1. Use of non-absorbable antibiotics to sterilize the gut: broad spectrum antibiotics such as polymyxin B have been used. This form of treatment is associated with significant toxicity [Nolan, et al., *Gastroenterology* 75:445–449 (1978)].
2. Use of bile salts and cholestryamine to bind endotoxin: associated with malabsorption of various nutrients and severe diarrhea [Cahil, *Br. J. Surg.* 76:590–595 (1983)].

(c). Monoclonal antibodies to endotoxin

Two different preparations of monoclonal IgM endotoxin antibodies have been evaluated In multi-center randomized placebo-controlled trials. Overall, no significant improvement in survival was detected in patients with gram-negative sepsis receiving the E5 murine monoclonal antibody [Greenman et al., *JAMA* 266:1097 (1991)]. A second study using a monoclonal human antibody showed a reduction in mortality only in patients who had demonstrable bacteremia. [Zeigler et al., *N. Engl. J. Med.* 324:429 (1991)].

It is abundantly clear therefore that there is a long recognized and continuing need for a completely different and unique approach for controlling and effectively reducing the levels of endotoxin circulating in vivo. In particular, were such a method shown to be non-toxic, able to be used long term for even several months duration, and able to provide for no major side effects, such a technique and approach would be recognised as a major advance long sought for in clinical practice and general usage. In so far as is presently known, however, such an effective and efficacious method has remained elusive and unavailable to date.

SUMMARY OF THE INVENTION

The present invention is a method for reducing the quantity of endotoxin circulating in the blood plasma of a living subject affected by an endotoxin-mediated state, said method comprising the steps of:

combining at least one persistent, acid-resistant, and colonizing Lactobacillus species with a biocompatible carrier to form a formulated preparation, said Lactobacillus species being able to persist within the gastrointestinal tract of the subject for not less than about 12 hours, being resistant to destruction by the acid pH from the stomach of the subject, and being able to colonize a mucosal surface within the gastrointestinal tract of the subject; and introducing said formulated preparation to the gastrointestinal tract of the living subject on as may occasions as are necessary to effect a reduction of endotoxin circulating in the blood plasma.

BRIEF DESCRIPTION OF THE FIGURES

The present invention may be more easily and completely understood when taken in conjunction with the accompanying drawing, in which.

DETAILED DESCRIPTION OF THE PRESENT INVENTION

The present invention is a method for reducing the quantity of endotoxin circulating in the blood plasma of a living subject who is affected by an endotoxin-mediated normal clinical condition or an abnormal medical state. The methodology employs a formulated preparation comprised of at least one persistent, acid-resistant, and colonizing Lactobacillus species and a biocompatible carrier which is introduced to the gastrointestinal tract (the stomach, the large intestine, and the small intestine) of the living subject on one or on multiple occasions such that a reduction in the quantity of endotoxin circulating in the blood plasma is effected. Although many species of Lactobacillus are conventionally known and are frequently found in various fermented food stuffs, almost all of the conventional strains are unsuitable and ineffectual because they commonly and uniformly fail to demonstrate the minimal requisite characteristics of showing long term persistence, being resistant to stomach pH concentrations of acid, and being able to colonize a mucosal surface of the gastrointestinal tract in vivo.

In this manner, the method of the present invention provides a range of previously unknown and unavailable major advantages and marked benefits to the affected subject. Among these are the following:

1. The present methodology is effective and of lasting duration in reducing the quantity of endotoxin(s) circulating in the blood plasma of the afflicted subject. The methodology and therapeutic Lactobacillus preparation is intended to be employed for human use primarily; but may clearly be effectively utilized in animals, particularly mammals, in veterinary therapeutic applications. The efficacy of the methodology is quickly established; is rapid in producing therapeutic effects and consequences; and may be employed on a regular regimen and fixed schedule or in a random, non-fixed routine on an as needed basis.

2. The present method may be employed efficaciously with any endotoxin-mediated pathological condition clinical disease state. It will be recognized and appreciated that the specific abnormal condition and pathology need not be directly caused by or originate through the transmigration of endotoxins from the gut of the afflicted subject. To the contrary, the migration of endotoxins into the body and the subsequent presence of endotoxins in the circulating blood of the afflicted subject may be a secondary consequence of the disease, the pathology of the abnormality, or an indirect result of the original stimulus, disorder, or cause. Nevertheless, so long as there is empirical evidence of endotoxin circulating within the blood plasma, the present methodology is suitable and proper for therapeutic application under those abnormal medical conditions. Accordingly, the present methodology is most suitable for use in a variety of human diseases and disorders including bowel ischemia, peritonitis, total body irradiation, colitis, portal vein occlusion, various forms of acute and chronic liver diseases, Crohn's disease, ulcerative colitis, necrotizing enterocolitis, and systemic infections of children and adults. A more general listing of abnormal disease states and pathological conditions has been given previously herein by Table A. Any and all of these endotoxin-mediated conditions are deemed to be suitable for therapeutic treatment using the present invention.

3. The methodology described herein is a non-toxic procedure and causes no major undesirable side effects. Unlike the many undesirable consequences and secondary effects (such as diarrhea, bone marrow suppression, renal failure, and gastrointestinal ulcers) caused by the use of neutralizing agents of macrophages; or the use of antibiotics, bile salts, and other binders; or the use of various antibodies specific for endotoxins; none of the conventionally known undesirable side-effects and secondary consequences appear concomitant with using the present methodology. Accordingly, many of the complications, procedures (intravenous infusions), and prolonged hardships (severe drug effects and reactions) common with conventionally known techniques are overcome with the present therapeutic method.

4. The methodology described herein may be used as a long term therapy, particularly with patients suffering from illnesses or abnormalities which require month or year long treatments. A representative example is the use of this therapeutic procedure with immunocompromised patients having a high risk of endotoxemia—which can be given this mode of therapy for several months' duration without fear of further compromising the immune system. Clearly, in these high-risk medical circumstances, the present therapeutic method is highly desireable and most preferred over all other conventionally known forms of therapy to achieve a continuous low-level of endotoxin in the circulating blood plasma.

5. The present invention may also be employed prophylactically, in advance of finding elevated endotoxin levels in the blood, to protect and ensure that a potential endotoxemia does not occur for both medically normal and medically abnormal subjects. Clearly, this prophylaxis mode of use may be employed in advance of a deteriorating medical condition—e.g., any cause of major disruption or deterioration of the mucosal barrier in the gastrointestinal system. A typical example of such prophylactic usage would be for those persons undergoing total body radiation—in which the immediate and long term consequences of radiation therapy are well recognized as markedly changing and altering the mucosal layers of the gut. The capability of protecting such patients against the high risk of endotoxemia as a secondary consequence of radiation therapy is an advantage and benefit which cannot be overstated in medical terms. Other conditions which could be similarly treated are patients admitted to the intensive care unit or patients with severe burns. These persons are at high risk for endotoxemia; and prophylactic therapy, free of side effects, could be potentially life saving.

6. The present invention is also useful for treating endotoxemia associated with severe physical exertion in medically normal living subjects. There is evidence that endotoxemia, probably resulting from increased intestinal absorption of endotoxin, occurs after severe physical exertion in both normal humans and animals. For example, in humans, increased levels of endotoxin in plasma were detected in medically normal persons after running the marathon. [Brock-Utne, et. al., *S. Afr. Med. J.* 73:533–536 (1988).] Similarly, increases in plasma endotoxin concentrations were seen in medically normal racehorses after races ranging in distance between 1000 and 2500 meters [Baker, et. al., *J. S. Afr. Vet. Assoc.* 49:63–66 (1988)]. Although the endotoxemia from exertion does not lead to a clinical disease state, it is believed that endotoxin, because of its ability to enhance oxygen consumption [Olson, NC, *Mol. Aspects Med.* 10:551:629 (1988)] contributes markedly to muscle fatigue. Thus, administration of the lactobacilli preparation prior to physical exertion will result in a decline in endotoxin concentrations in normal persons and reduce the severity of muscle fatigue. Moreover, since high endotoxin levels persist up to three weeks after the time of physical exertion, administration of the lactobacilli preparation even after the period of exertion should prove to be beneficial during the recovery period.

7. The present methodology requires only that the Lactobacillus formulated preparation be introduced to the gastrointestinal tract of the afflicted subject. The most preferred route of administration is per oral; this preferred mode of administration presumes, however, that the subject is capable of swallowing and is medically able to endure the ingestion of solid food as such. Accordingly, a variety of other routes of administration and introduction to the afflicted subject are envisioned and included as a intrinsic part of the methodology. Thus, for subjects undergoing severe trauma or surgical procedures, intragastric and intracolonic routes of administration typically using catheters or other infusion apparatus may be usefully employed. In this manner, therefore, the Lactobacillus formulated preparation may be introduced at a very early stage in the disease progression and pathology to the living subject; and major intervention and therapy may be had prior to onset of advanced stage disease or the acute or critical manifestations on symptoms of the disease state.

To aid in fully understanding and properly appreciating the present method in all its various aspects and applications, the detailed disclosure of the present invention will be presented in individual descriptive sections seriatim. These include: a description of the characteristics and properties of the Lactobacillus species which are minimally necessary and as well as those most preferred with the present methodology; a disclosure of various biocompatible carriers suitable and intended for use when formulating the therapeutic preparation; a representative abnormal state illustrating the cascade of events mediated by endotoxin in the circulating blood; a disclosure of means for detecting endotoxin in the circulating blood plasma; and a typical range of elevated endotoxin values found in the plasma under different abnormal disease states; a preferred protocol for introducing the formulated preparation into the gastrointestinal tract; a presentation of illustrative disease states and representative treatment procedures employing the present methodology; and a presentation of experiments and empirical data demonstrating the in vivo efficacy of the present invention.

I. The Formulated Preparation.

The methodology which is the present invention requires and utilizes a formulated preparation comprised of two component parts: a persistent, acid-resistant and colonizing Lactobacillus strain or species; and a biocompatible carrier. Each of these will be described individually.

A. The Properties and Characteristics of the Lactobacillus Species.

The genus Lactobacillus is widely distributed in nature. Several species, including *Lactobacillus acidophilus*, are components of the normal intestinal flora of healthy humans. Other species, such as *Lactobacillus bulgaricus* and *Lactobacillus casei*, are found in dairy products as well as in various fruits and vegetables. Moreover, some research studies have shown that when lactobacilli are implanted in the intestinal tract, there appears to be a suppressive effect on other members of the microflora. For example, it has been reported that in experimental animals given lactobacilli, antibiotic associated diarrhea and colitis has been controlled; that the metabolic activation of carcinogens by the intestinal flora of humans and animals is suppressed; and that chemically induced colon cancer is reduced. These reports are represented by the following publications: Gilliland, S. E., *FENS Microbiology Reviews* 87:175–188 (1990); *Nutritional Reviews* 42:374–375 (1984); Klebanoff et al., *J. Infect. Dis.* 164:94–100 (1991); Rammelsberg, N. and F. Radler, *J. Appl. Bact.* 69:177–184 (1990); Gorbach S. L., *Annals Of Medicine* 22:37–41 (1990); and the references cited within each one of these publications individually.

Almost all of these conventionally known species of Lactobacillus are highly sensitive to acid pH values such as those found in the stomach; have no capability or survival value for persisting within the gastrointestinal tract for a length of time substantially greater than about 6 hours at most; and have no colonizing capabilities for the gut as a consequence of these deficiencies. The commonly shared failure of attributes, properties, and characteristics has been explicitly observed and empirically determined by investigators who identified the fate of ingested lactobacilli in the proximal small intestine [Robins-Browne, R. N. and M. M. Levine, *Am. J. Clin. Nutr.* 34:514–519 (1981)]. These investigators reported that freeze-dried commercial preparations of *Lactobacillus acidophilus* and *Lactobacillus bulgaricus* dissolved in skim milk and ingested by fasting and non-fasting persons did not survive within the gut for an extensive period of time. In particular, it was noted that Lactobacillus entered the small intestine and persisted in elevated numbers for only about 3 hours in fasting subjects and only up to 6 hours in nonfasting individuals; and that after 4 hours, the lactobacilli count in fasting volunteers had returned to original base-line levels. The repeated failure to survive in the gut are representative generally of and are commonly shared by species throughout the genus Lactobacillus.

In contrast and in opposition to almost all the conventionally known strains and species of Lactobacillus, the strains and species suitable for use in the present methodology must have present at least three individual characteristics and attributes; and preferably provide a number of other properties and characteristics which are highly desireable for those bacterial strains used within the present methodology. The requisite and essential attributes as well as the highly preferred and more desireable properties of the species are presented by Table 1 below.

TABLE 1: Essential and Preferred Characteristics of Lactobacilli (Normal or Genetically Engineered)

1. The lactobacillus strain must be able to colonize the human bowel and persist in the gastrointestinal tract after administration into the GI tract (either orally, via colonoscopy, intragastric tube or other means). The lactobacilli should ideally persist in the GI tract for at least 12–24 hours, but preferably remain viable for longer periods up to several days.
2. The Lactobacillus strain should be resistant to destruction by the acid pH In the stomach as well as tolerant of other digestive juices such as bile, pancreatic juice, etc.
3. The Lactobacillus strain should be able to produce hydrogen peroxide which would be of potential use in destruction of pathogenic endotoxin producing bacteria.
4. The lactobacilli should suppress the growth of endotoxin (lipopolysaccharide) producing bacteria. This can occur by several mechanisms which may include competition for nutrients and elaboration of antimicrobial substances.
5. The lactobacilli should be able to prevent attachment of endotoxin producing bacteria to the intestinal wall.
6. The Lactobacillus strain, in order to colonize a mucosal surface must possess certain properties including adhesion, competitive exclusion ability and inhibitor production.
7. The lactobacilli should produce antimicrobial substances and/or produce proteinaceous antagonistic substances (bacteriocins). The production of these substances aids in preventing the growth of gram-positive and gram-negative bacteria in the intestines, thereby reducing endotoxin formation.

For purposes of the present invention, the best mode of practicing the method which is the present invention will employ a newly isolated strain of a species of Lactobacillus of human origin designated "GG" which has been empirically evaluated and shown to provide both the requisite as well as the preferred characteristics for use herein. The attributes and properties of Lactobacillus GG have been reported; and this specific strain is deemed to be publicly available upon demand either by direct isolation from humans or by purchase from commercial sources or research laboratories. Representative publications describing the isolation, attributes and properties, and reported investigations of Lactobacillus GG include the following: [Goldin et al., *Digestive Diseases and Sciences* 37:121–128 (1992) and the references cited therein; Silva et al., *Antimicrobial Agents and Chemotherapy* 31:1231–1233 (1987); and Gorbach et al., *Lancet* 1:1519 (1987)].

Lactobacillus GG is the most preferred and desireable species for use to date when formulating the preparation for use with the present methodology. It must be emphasized that this most preferred strain is a naturally occurring isolate from human subjects; and that other species having at least the minimal requisite and essential criteria of persisting within the gut for at least 12-24 hours, for resisting acid pH levels found within the stomach, and for colonizing the mucosal layer of the gut can and will be found as needed or required. In addition, the present advances and knowledge regarding recombinant DNA variants allow for the individual identification and selection of genes in the naturally occurring species which then can be artificially introduced into other previously unsuitable strains of Lactobacillus— thereby rendering them with the essential characteristics in a completely synthetic and artificial creation. Accordingly, both naturally occurring and chemically synthesized strains of Lactobacillus and/or strains taxonomically identified as being other genera yet having and demonstrating the requisite essential attributes and properties, are all deemed to be encompassed by and included within the scope of the present invention.

B. Biocompatible Carriers.

A wide variety of different carrier compositions may be employed so long as the chosen compound or substance is biocompatible, non-toxic, and nonirritating to the intended recipient. Since the most preferred route of introduction and administration is per oral, highly desireable carriers include milk, milk fractions, milk derivatives, milk concentrates, and milk fermentations. Alternatively, freeze-dried bacterial cultures in capsule format are suitable for use; and other conventionally known tablet, particle, and gel carriers are equally acceptable. Accordingly, so long as the subject is able to ingest solid matter and is able to swallow, these milk products and solids are the carriers of choice.

Alternatively, the carrier may typically be comprised of a solid or semi-solid petrolateum; and include such excipients as glycerol, alcohol, glycols, fatty alcohols, triglycerides, fatty acid esters, or mineral oils. In addition, materials such as anti-oxidants, humectants, viscosity stabilizers and the like, may be included in the preparation. In addition and particularly in instances of intragastric or intracolonic routes of administration, where milk product and solid carriers are not ideal, the requisite Lactobacillus species may be dispersed in an aqueous fluid carrier such as sterile physiological saline or 5% dextrose solutions commonly used with injectibles. In such instances, it is highly desireable that the carriers be prepared in sterile form, whether in multiple or single dose formats.

C. A Preferred Formulated Preparation.

One most desirable formulated preparation of Lactobacillus GG is as a frozen concentrate. The organism is grown in MRS broth which is then centrifuged at high speed. The pellet is washed and suspended in the fluid of choice—e.g., skim milk. A final concentration of between $1 \times 10^9$ CFU/ml and $2 \times 10^9$ CFU/ml should be attained; the counts can be verified on LBS agar. The suspension is desirably dispersed as 1 or 2 ml aliquots which are then frozen at $-80°$ C. Prior to use, these concentrates are defrosted and mixed with the appropriate biocompatible carrier. Daily doses to be administered should range between $1 \times 10^{11}$ CFU to $2 \times 10^{12}$ CFU/day, for the typical patient. However, the full dosage range can vary from about $10^8$–$10^{14}$ CFU per day.

II. Preferred Protocol for Introducing Lactobacillus Formulated Preparations Into the Gastrointestinal Tract 1. Between $1 \times 10^{10}$ and $2 \times 10^{11}$ colony forming units ("CFU") of the Lactobacillus species are preferably prepared either as a frozen concentrate or as fermented milk in the manner described previously herein.

2. The above preparation is introduced into the gastrointestinal tract preferably via the oral route, but other routes of administration (intragastric, intracolonic) are also acceptable. 3. The chosen dose is given ideally once each day but may vary according to the disease process for which the Lactobacillus is being used. For example, in impending sepsis, high concentrations (above $2 \times 10^{11}$ CFU) given more often (every 4-6 hours) may be appropriate since endotoxin levels are high in these patients. More chronic diseases such as alcoholic cirrhosis may require lower concentrations ($<10^{11}$ CFU) at less frequent (once every 2-3 days) administration. In general, however, the broad range of lactobacilli dosages are from a low of about $10^8$ CFU/day to a high of about $10^{14}$ CFU/day in one or more administrations.

4. The appropriate dose of Lactobacillus can be monitored by analysis of fecal specimens. On a regular basis (once a day in acute conditions or once a week in chronic conditions), an aliquot of fecal material is cultured in agar. After incubation, the agar plates are counted and the presence of Lactobacillus will be confirmed by conventional sugar fermentation tests. The presence of significant Lactobacillus in feces will be evidence for survival of the Lactobacillus strain within the gastrointestinal tract.

5. Disease activity in patients receiving Lactobacillus will be monitored; this will clearly depend on which disease process is being altered or treated.

III. A Representative Disease State.

It is desireable to describe the cascade of events for a representative disease and pathological state in order to better demonstrate the relationship between endotoxin and the endotoxin-mediated consequences of the pathological condition. A useful example is sepsis, the sepsis syndrome and septic shock, all of which commonly occur as abnormal disease states. A summary of the successive events occurring in this state is therefore given by Table 2 below.

TABLE 2

Sepsis, Sepsis Syndrome and Septic Shock: Cascade of Events

TABLE 2-continued

Sepsis, Sepsis Syndrome and Septic Shock: Cascade of Events

In this representative example, the spectrum of gram-negative infections and endotoxemia includes local infections, sepsis, the sepsis syndrome and septic shock. Endotoxin release from the cell wall of gram negative organisms (which trigger a cascade of host mediators) leads to a progressively more severe systemic response. Although the pathogenesis of sepsis has not been fully elucidated and is recognized as being extraordinarily complex, it has become clear that the initiating event in the sepsis cascade is the local release of endotoxin and its subsequent absorption/release into the circulation. Note that any treatment method which is to be effective must be given as early as possible in the sepsis cascade. Efficacious reduction of endotoxin levels in the blood circulation by the method described herein occurs at an early stage in the cascade.

IV. Evidence of Endotoxin Circulating in the Blood Plasma

The method of the present invention is effective in reducing the quantity of endotoxin circulating in the blood plasma of the medically abnormal subject. Occasionally, the abnormal medical condition suitable for therapeutic treatment using the present invention may require that the clinician or physician be able to detect the presence of endotoxin in the blood; and further, if the physician so chooses, to determine that the quantity of endotoxin in the blood plasma is being reduced as a consequence of practicing the present invention. Alternatively, in the absence of endotoxin measurements, the clinical symptoms and signs can be used as an indicator of efficacy for the treatment. However, a general description of the means for detecting endotoxins from a sample is described below; and a typical range of elevated endotoxin values found in the blood plasma under different abnormal disease states is given by Table 3 below.

Detection of Endotoxin

For many years, only cumbersome animal tests were available to measure indirectly the presence of endotoxin. Among the many techniques used, those in common use included chick embryo lethality, histamine sensitivity and induction of fever. The development of the Limulus lysate assay made all previously used methods for detecting endotoxin obsolete [Levin et al., J. Lab. Clin. Med. 75:903-911 (1970)]. Levin showed that small amounts of lipopolysaccharide (endotoxin) activated the clotting system found in amoebocytes of the horseshoe crab, Limulus polyphemus.

The most significant advance for detection of endotoxin in humans has been the introduction of chromogenic substrates for the Limulus clotting enzymes which has allowed measurements in the picogram range [Iwanga et al., Homeostasis 7:183-188 (1978)]. This assay is more sensitive and specific than previously used assays.

All blood samples are mixed with endotoxin-free heparin (Sigma Chemical Co., St. Louis, Mo.) producing a final concentration of 15 units heparin per ml blood. The specimen is placed on ice and transported immediately to the laboratory. Plasma is then immediately separated in a refrigerated centrifuge and then stored at $-20°$ C. to $-80°$ C. for subsequent analysis.

Maximal detection of low concentrations of endotoxin by the chromogenic assay is obtained by diluting the plasma fourfold with 0.15 mol/L NaCl followed by heating at 60° C. for 30 minutes. The glassware used in both collection of blood specimens and in the subsequent assay should be rendered endotoxin free by heating at 180° C. for 24 hours.

The assay is performed according to manufacturers instructions. In a typical assay, the heated and diluted plasma is reconstituted with pyrogen free water and incubated at 37° C. for 45 minutes. At the end of this period, the chromogenic substrate is added to the test mixture followed by further incubation at 37° C. for 10 minutes. The reaction is stopped by addition of 0.15 ml of 50% acetic acid. The absorbance is read at 405 nm in a spectrophotometer.

A standard curve is prepared for each batch of samples tested using endotoxin stock solution (E. coli lipopolysaccharide B, 055:B5). A reagent blank is included in each assay run. The blank consists of test plasma, limulus lysate and substrate but with acetic acid added at Time 0 min. This allows measurement of the intrinsic absorbance of the test mixture. The net increase in absorbance in a patient sample is attributed to the presence of endotoxin.

TABLE 3

| ABNORMAL DISEASE STATE | TYPICAL ENDOTOXIN LEVELS | RELATIONSHIP BETWEEN ENDOTOXIN LEVELS AND DISEASE SEVERITY | REFERENCE |
| --- | --- | --- | --- |
| Septic Shock | 440 ± 120 pg/ml (mean ± SD) | Presence of endotoxemia correlates with cardiac depression and multiple organ failure | Danner et al., Chest 99:169-75 (1991). |
| Systemic Meningoeoccal Disease | <25->10,000 pg/ml | Higher endotoxin levels are associated with increased fatality in patients with | Brandtzaeg, et al., J. Infect. Dis. 159:195-204 |

TABLE 3-continued

| ABNORMAL DISEASE STATE | TYPICAL ENDOTOXIN LEVELS | RELATIONSHIP BETWEEN ENDOTOXIN LEVELS AND DISEASE SEVERITY | REFERENCE |
|---|---|---|---|
| | | systemic meningoeoccemia. <br> Endotoxin Level    % Fatality <br> <25    0 <br> 25–700    14 <br> 700–10,000    27 <br> >10.000    86 | (1989). |
| Acute Pancreatitis | 0–563 pg/ml | Endotoxemia was more common in non-survivors than in survivors. Range of endotoxin levels in non-survivors was higher (173–563 pg/ml) than in survivors (0–165). | Exley, et al., Gut 33:1126–1128 (1992). |
| Liver Transplantation | 13.4–295 pg/ml | High endotoxin levels pre-operatively and during the anhepatic phase were associated with graft failure and high mortality. | Yokoyama et al., Transpl. Proc. 21:3833–3841 (1989). |
| Liver Transplantation | 41–173 pg/ml | Severity of endotoxemia correlated with need for perioperative platelet transfusion and one month case fatality. | Miyata, et al., Lancet 2:189–191 (1989). |
| Heatstroke | 860 ± 119 pg/ml | Endotoxin levels correlate with body temperature. | Bouchama et al., J. Appl. Physiol. 70:2640–2644 (1991). |
| Cirrhosis (various causes, including alcoholic, infectious, etc.) | Hepatic vein: 75.3 ± 110.4 pg/ml <br> Peripheral vein: 30.7 ± 58.3 pg/ml | Endotoxin levels correlate with severity of liver dysfunction. | Lumsden, et al, Hepatology 8:232–236 (1988). |

V. Illustrative Disease States and Representative Individual Treatment Procedures A preferred general protocol for performing the method of the present invention has been provided herein previously. In addition, however, because the abnormal disease states suitable for treatment using the present invention are often markedly different from one another; and because there are specialized practices and procedures highly desireable in one pathological state which may be omitted entirely in another abnormal condition or disease state, a more detailed restatement of the more general protocol is provided herein after. It will be expressly understood, however, that these detailed individual treatment protocols, are merely representative of those suitable for use with each individual abnormal condition and pathology. Moreover, the user may, for his own individual reasons or necessity, adopt any other individual detailed protocol in place of the one identified below for that specific disease or disorder; and substitute at will any and all parameters as needed or desired in the best interests of his patient. With these considerations in mind, a more detailed procedure for specific abnormal and disease states is given below.

A. Sepsis

1. Patient has high risk for developing sepsis; e.g.—immunocompromised patient or if patient has developed early signs of sepsis (tachypnea, tachycardia).

2. Give patient first dose of Lactobacillus therapeutic preparation and then every 4–6 hours depending on severity of illness/endotoxin levels.

3. Follow fecal counts of Lactobacilli (if not detected, increase frequency of dose) administration.

4. Follow endotoxin levels in plasma and/or clinical signs and symptoms.

5. Monitor patient response, i.e., temperature, respiratory rate, heart rate, urine output.

6. If clinical improvement is seen or if endotoxin levels decrease significantly, reduce the frequency of lactobacilli therapeutic preparation administration.

Alcoholic Liver Diseases

1. Give patient Lactobacillus concentrate once daily.

2. Follow fecal counts of lactobacilli (if not detected, increase frequency of dose).

3. Monitor endotoxin levels.

4. Monitor disease activity by evaluating liver enzymes, liver pathology by biopsy, nutritional status. The frequency of dose administration will depend on the stage of alcoholic liver disease—i.e., hepatitis or cirrhosis. For hepatitis a greater frequency of dosage administration will be necessary.

C. Bowel Ischemia

1. In a patient with clinical features suggestive of bowel ischemia, intensive and aggressive lactobacilli preparation therapy is recommended.

2. A one-two hour interval is recommended between administrations of lactobacilli doses.

3. Frequent endotoxin monitoring is recommended.

4. Monitor white cell count and body temperature which may indicate onset of peritonitis. If an improvement in these parameters is seen, reduce frequency of lactobacilli administration to every 4–6 hours.

D. Acute Renal Failure

1. Give first dose of lactobacilli formulated preparation when patient is admitted with renal failure (high serum creatinine, oliguria).

2. Follow patient's clinical and laboratory parameters, evaluating kidney function.

3. If no improvement is seen in endotoxin levels within 24 hours, give second dose of lactobacilli preparation.

4. Follow fecal counts of lactobacilli (if not detected, increase the frequency of administering the dose).

E. Adult Respiratory Distress Syndrome (ARDS).

1. At the first sign of respiratory distress, give first dose of lactobacilli formulated preparation.

2. Measure endotoxin levels and parameters of tissue oxygenation.

3. If ARDS is associated with sepsis, more frequent dosing (every 2–3 hours) may be necessary.

4. Follow fecal counts of lactobacilli to determine adequacy of dose and frequency.

F. Abdominal/Chest Trauma

1. Administer the lactobacilli preparation when patient is first admitted to trauma unit.

2. Measure endotoxin levels in the blood.

3. If endotoxin level is >100 pg/ml, administer lactobacilli preparation every hour.

4. If endotoxin is <100 pg/ml, reduce frequency of dose administration to every 4–6 hours.

G. Radiation Injury

1. Radiation causes intestinal alterations that lead to transmigration of endotoxin into the blood stream.

2. Before a patient is given the first course of radiation therapy, it may be necessary to give lactobacilli preparation daily for a 1–2 week period to reduce the concentrations of endotoxin producing bacteria.

3. Measure endotoxin levels in the blood after the first course of radiation therapy.

4. If significant endotoxemia occurs (>20 pg/ml), increase the frequency of the lactobacilli preparation administration to six doses hourly before the second course of therapy.

H. Graft vs. Host Disease (GVH)

1. While GVH-mediated disease is mostly commonly seen in bone marrow transplantation, it also occurs following lung and bowel transplantation.

2. In patients with acute GVH disease, administer lactobacilli formulated preparation when clinical features appear initially (e.g., skin rash).

3. Administer lactobacilli doses every 4–6 hours and follow endotoxin levels and fecal lactobacilli counts.

4. In patients with chronic GVH disease, initial daily therapy with lactobacilli preparation is required with subsequent reduction in frequency of dosing when clinical improvement and/or reduction in endotoxin levels are seen.

In those patients with chronic GVH disease who develop recurrent infections, an increased frequency of dosing may be necessary.

I. Toxic-Shock Syndrome (TSS)

1. In patients with clinical features of TSS (rash, fever, desquamation of palms/soles), give lactobacilli preparation once every hour.

2. Follow patient to determine development of hypotension and involvement of other organ systems.

3. Follow endotoxin levels and fecal lactobacilli counts.

4. If endotoxin levels decline or patient shows improvement, reduce the frequency of lactobacilli formulated preparation administration.

J. Immunocompromised Patients with or without Fever

1. Patients who are immunocompromised secondary to a chronic disease process, e.g., malignancy, immunosuppressive drugs, should be given long-term lactobacilli preparation treatment.

2. The treatment can be given on a weekly basis with follow up of fecal lactobacilli counts.

3. If such a patient develops a fever or signs of infection, change weekly therapy administration to once every 12–24 hours.

K. Neonatal Necrotizing Enterocolitis

1. In a patient who is at risk of developing necrotizing enterocolitis, e.g., premature infant in neonatal intensive care unit or who develops suggestive signs and symptoms, begin hourly administration of lactobacilli formulated preparation.

2. Follow plasma endotoxin levels and fecal lactobacilli counts.

3. If improvement is seen, reduce the frequency of lactobacilli preparation administration to every four hours.

4. If patient develops oliguria, jaundice, continue hourly administration of the lactobacilli preparation.

L. Liver Transplantation

1. Measure endotoxin levels in the blood when liver recipients are being worked up for transplantation.

2. If endotoxin is detectable in serum, administer a first dose of lactobacilli formulated preparation and continue such administrations until lactobacilli are detected in feces.

3. During the phase of removal of native liver, anhepatic phase and placement of graft, administer lactobacilli via an orogastric tube at one hour intervals. Measure endotoxin levels at hourly intervals.

4. If at the end of the anhepatic period, the endotoxin level is >100 pg/ml, continue hourly administration of lactobacilli formulated preparation until the endotoxin level is <100 pg/ml. Then, the frequency of dosing can be gradually reduced.

M. Acute Pancreatitis

1. Measure the endotoxin level of the blood in patient admitted with acute pancreatitis.

2. If the endotoxin level is >20 pg/ml, start administering the lactobacilli formulated preparation at hourly intervals via orogastric or nasogastric tube.

3. Determine endotoxin levels in the blood hourly.

4. Monitor severity of the disease by following parameters which herald onset of shock: hypotension, oliguria, etc.

5. In cases of impending shock associated with high levels of endotoxin, continue the hourly frequency of lactobacilli preparation administration.

VI. Experiments And Supporting Empirical Data.

A series of experiments and resulting data are provided below which demonstrate and reveal both the utility and efficacy of the present invention. While the experiments and resulting data confine themselves to specific test circumstances and disease conditions, it will be recognized and appreciated that neither the experimental design nor the empirical data resulting therefrom limit or restrict the present invention in any meaningful manner whatsoever. To the contrary, the experiments and data presented are merely representative and illustrative of the therapeutic methodology on the multiple applications and use circumstances under which the invention may be used advantageously and beneficially. In addition, the experiments and empirical data presented below demonstrate and disclose the parameters, values, and essential effectiveness of the subject matter as a whole comprising the present invention.

Materials and Methods:

Animal Model Male Wistar rats between 225 and 250 grams were fed by continuous infusion of liquid diet through permanently implanted gastric tubes as described in the literature [French et al., *Alcoholism Clin. Exp. Res.* 10:135–195 (1986); Tsukamoto et al., *Hepatology* 6:814–822 (1986)]. The average caloric distribution for each nutrient when the animals were receiving maximal amounts of ethanol was: 25% of total calories as fat (corn oil), 21% as protein, 12% as carbohydrate and 42% as ethanol. Two groups of animals were studied; one group (n=6) was given the diet as above i.e. corn oil as source of fat and ethanol. The amount of ethanol given was modified to maintain high levels of blood alcohol (150 to 300 mg/dL). This amount was initially 8 gm/kg/day and increased up to 17 gm/kg/day as tolerance developed. All rats had free access to water and non-nutrient fiber. The second group was pair-fed the same diet as the first group but in addition was given, every morning, via the same intragastric tube delivering ethanol and diet, a bolus of Lactobacillus species strain GG (Lactobacillus GG) concentrate. The concentrate had $2 \times 10^{10}$ CFU/ml and was prepared as previously described [Goldin et al., Dig. Dis. Sci. 37:121–128 (1992)]. Immediately prior to use, the concentrates were defrosted and mixed with sterile water. A daily dose of $10^{10}$ CFU/rat was given. All animals were sacrificed at 1 month after the start of feeding.

Histologic and Biochemical Analyses

A small sample of liver was obtained at sacrifice and formalin-fixed. The severity of liver pathology was assessed as follows: steatosis (the percentage of liver cells containing fat): $1+ = 0$–$25\%$ of cells containing fat, $2+ = 25$–$50\%$, $3+ = 51$–$75\%$, $4+ = >75\%$. Inflammation and necrosis were scored as one focus per low power field $= 1+$, two or more foci $= 2+$. The pathology score was calculated by adding the individual parameter scores.

Blood was collected in appropriate tubes at sacrifice, immediately centrifuged and stored at $-70°$ C. until analysis. Endotoxin in plasma was measured using a synthetic chromogenic assay (Whitaker Bioproducts Inc., Walkerville, Md. 21792). The glassware used in the assays was rendered endotoxin-free by heating at $180°$ C. for 24 hours. Pyrogen-free water was supplied by the manufacturer. The procedures used in the testing for endotoxin conform with those described in the Food and Drug Administration guidelines. This assay provides better quantitation and is more sensitive and specific than previous gelation assays. Blood alcohol was measured using the alcohol dehydrogenase assay (Sigma Chemical Co., St. Louis, Mo.). Data are expressed as mean $\pm$SE. Different groups were compared using the Student t test.

Figure 1:
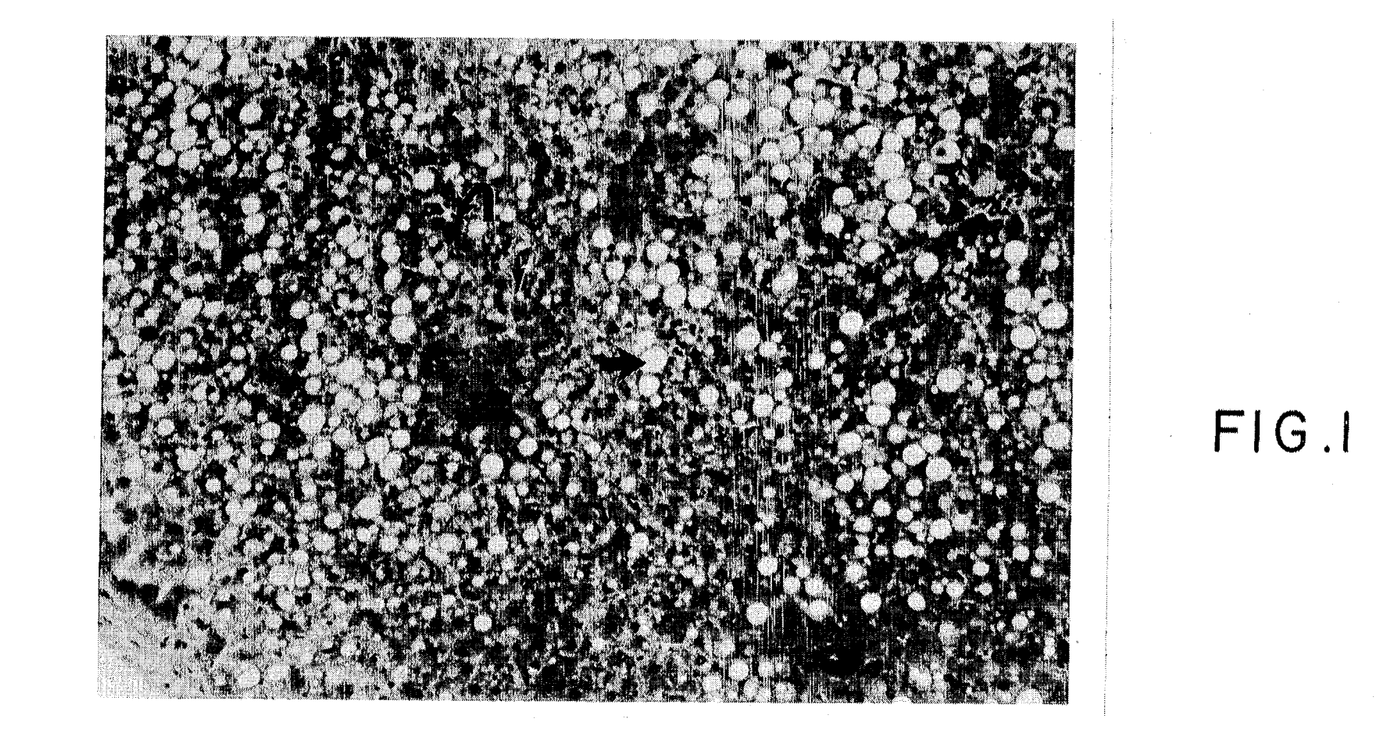
FIG. 1 is a photograph of a hematoxylin and eosin stained liver specimen, at magnification ×155, taken from a rat fed alcohol and corn oil for one month and showing the presence of macrovesicular fat (large arrow), microvescular fat (small arrow), an area of hepatocyte necrosis (curved arrow), and inflammatory infiltrate (arrowhead)
Figure 2:
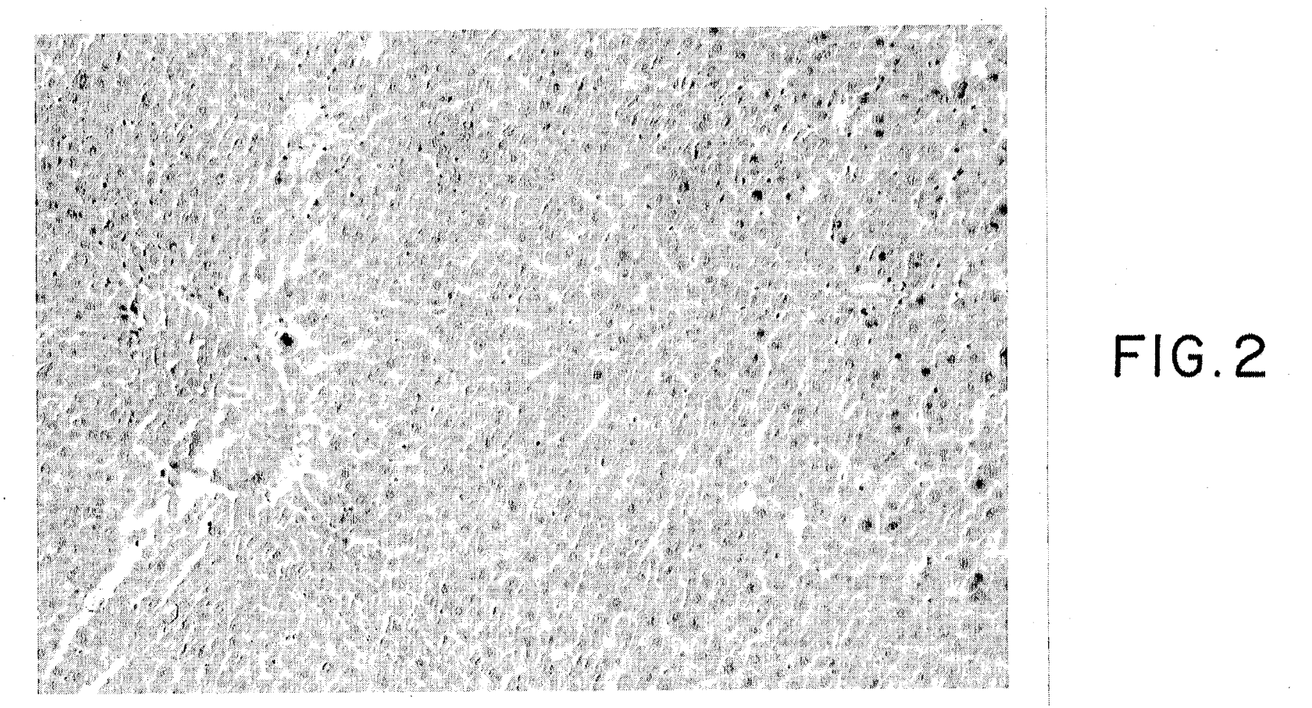
FIG. 2 is a photograph of a hematoxylin and eosin stained liver specimen, at magnification ×155, taken from a rat fed alcohol, corn oil and a persistent, acid-resistant, and colonizing Lactobacillus species for one month and showing the presence of a normal histology with no fatty change, necrosis, or inflammation.

Results:

The rate of weight gain and blood alcohol values were not significantly different in the two groups. The details of pathologic severity and plasma endotoxin levels is shown in Table E1. The mean $\pm$SE of the pathologic score in the corn oil-ethanol group is significantly higher ($3.4 \pm 0.85$) than in the Lactobacilli group ($0.5 \pm 0.3$) ($p < 0.01$). FIG. 1 shows an example of pathologic changes seen in one of the animals fed corn oil and ethanol. The protective effect of lactobacilli is reflected in FIG. 2 which shows absence of any pathology in the liver of lactobacilli fed rats. The less severe pathology in the lactobacilli group is accompanied by lower endotoxin levels (Table E1). In one of the animals in the lactobacilli fed group that developed a 2+ fatty change, the endotoxin level was about 3 times the mean level seen in the same group.

TABLE E1

Comparison of severity of pathologic changes and plasma endotoxin levels in the corn oil–ethanol fed group and corn oil-ethanol-lactobacilli group.

| | Corn oil + ethanol | | | | Corn oil + ethanol + lactobactili | | | |
|---|---|---|---|---|---|---|---|---|
| Animal No. | Pathology | | | Endotoxin pg/ml | Animal No. | Pathology | | | Endotoxin pg/ml |
| | F | N | I | | | F | N | I | |
| 1 | 1+ | 1+ | 1+ | 60.6 | 1 | 2 | 0 | 0 | 21.8 |
| 2 | 0 | 0 | 0 | 33 | 2 | 0 | 1 | 0 | 7.7 |
| 3 | 3+ | 2+ | 2+ | 62.5 | 3 | 0 | 0 | 0 | 3.3 |
| 4 | 3+ | 1+ | 0 | 52.6 | 4 | 0 | 0 | 0 | 8.3 |
| 5 | 1+ | 0 | 0 | 13.5 | 5 | 0 | 0 | 0 | 0.8 |
| 6 | 2+ | 1+ | 1+ | 67.5 | 6 | 0 | 0 | 0 | 4.6 |

F = fatty liver;
N = necrosis;
I = inflammation

The mean $\pm$ SE of the composite pathology score for the corn oil-ethanol animals ($3.4 \pm 0.85$) is significantly different from the score in the lactobacilli group ($0.5 \pm 0.30$, $p < 0.01$). Also, the endotoxin levels are lower in the lactobacilli group ($8.4 \pm 2.9$ pg/ml) compared to the corn oil-ethanol group ($48.3 \pm 7.8$ pg/ml) ($p < 0.01$).

Conclusions:

The use of lactobacilli in a biocompatible carrier provides a non-toxic and non-invasive method of altering gut contents. The results show that the reduction in plasma endotoxin levels in lactobacilli-fed animals is also accompanied by a reduction in the severity of liver injury. The Lactobacillus GG species remains in the gastrointestinal tract for at least 4 days; furthermore, the organism is resistant to acid and bile and elaborates an antimicrobial substance. In conclusion, the use of strains of lactobacilli that survive in the intestinal tract offers a non-toxic form of therapy able to reduce endotoxin levels in the plasma.

The present invention is not to be restricted in form nor limited in scope except by the claims appended hereto.

What we claim is:

1. A therapeutic method for reducing the quantity of endotoxin circulating in the blood plasma of a mammal, said method comprising the steps of:

combining Lactobacillus GG with a biocompatible carrier to form a preparation, wherein said Lactobacillus GG is able to persist within the gastrointestinal tract of the mammal for not less than 24 hours, is resistant to destruction by the acid pH from the stomach of the mammal, and is able to colonize a mucosal surface within the gastrointestinal tract of the mammal; and administering said formulated preparation to the gastrointestinal tract of the mammal in an amount effective for causing a resulting reduction in the quantity of endotoxin circulating within the mammal's blood plasma.

2. The method as recited in claim 1 wherein said Lactobacillus GG is able to release hydrogen peroxide while within the gastrointestinal tract of the mammal.

3. The method as recited in claim 1 wherein said Lactobacillus GG is able to suppress the growth of endotoxin producing bacteria within the gastrointestinal tract of the mammal.

4. The method as recited in claim 1 wherein said Lactobacillus GG is able to prevent attachment of endotoxin producing bacteria to the intestinal wall of the mammal.

5. The method as recited in claim 1 wherein said Lactobacillus GG is able to produce bacteriocins within the gastrointestinal tract of the mammal.

6. The method as recited in claim 1 wherein said Lactobacillus GG is able to produce at least one antimicrobial substance within the gastrointestinal tract of the mammal.

7. The method as recited in claim 1 wherein said biocompatible carrier is selected from the group consisting of liquids, solids and semi-solids.

8. A therapeutic method for reducing the quantity of endotoxin circulating in the blood plasma of a mammal afflicted with alcoholic liver disease, said method comprising the steps of:

combining Lactobacillus GG with a biocompatible carrier to form a preparation, wherein said Lactobacillus GG is able to persist within the gastrointestinal tract of the mammal for not less than 24 hours, is resistant to destruction by the acid pH from the stomach of the mammal, and is able to colonize a mucosal surface within the gastrointestinal tract of the mammal; and administering said formulated preparation to the gastrointestinal tract of the mammal in an amount effective for causing a resulting reduction in the quantity of endotoxin circulating within the mammal's blood plasma.

* * * * *